United States Patent [19]

Collart et al.

[11] Patent Number: 5,665,583

[45] Date of Patent: Sep. 9, 1997

[54] METHODS AND MATERIALS RELATING TO IMPDH AND GMP PRODUCTION

[76] Inventors: Frank R. Collart, 1056 Crestwood La., Bolingbrook, Ill. 60439; Eliezer Huberman, 424 Sunset Ave., LaGrange, Ill. 60525

[21] Appl. No.: 232,302

[22] Filed: Aug. 12, 1988

[51] Int. Cl.$^6$ .................... C12N 15/52; C12N 1/21; C12N 15/63; C12N 15/85

[52] U.S. Cl. ............ 435/191; 435/89; 435/172.3; 435/252.3; 435/252.33; 435/320.1; 435/358; 435/325; 536/23.2; 536/23.5

[58] Field of Search ............... 435/89, 191, 172.3, 435/320.1, 252.3, 252.33, 240.1, 240.2; 536/23.2, 23.5

[56] References Cited

PUBLICATIONS

Tiedeman et al., 1985, NAR, vol. 13(4):1303–1316.
Jaye et al., 1983, NAR 11(8):2325–2335.
Old et al., in Principles of Gene Manipulation, Blackwell Scientific Publ., Third edition, (1985) pp. 10–13, 127–202, 288–293).
Atkins, et al., Arch. Biochem. Biophys., 236:807–814 (1985).
Boyum, A., Scand. J. Clin. Lab. Invet., 21(97):51–55 (1968).
Caplan, A., et al., Science, 222:815–821 (1983).
Chirgwin, et al., Biochemistry, 18:5294–5299 (1979).
Cohen, M.B., et al., Cancer Res., 43:1587–1591 (1983).
Cohen, M.B., et al., J. Biol. Chem., 256:8713–8717 (1981).
Collart, et al., Mol. Cell. Biol., 7:3328–3331 (1987).
Cooney, et al., Anal. Biochem., 130:339–345 (1983).
Davis, et al., Molecular Biology, 18–1:286–289 (1986).
Devereux, et al., Nuc. Acids. Res., 12:387–395 (1984).
Duan, et al., Cancer Res., 47:4047–4051 (1987).
Elliott, et al., Mol. Cell. Biol. 5:236–241 (1985).
Feinberg, et al., Anal. Biochem., 132:6–13 (1983).
Franklin, et al., Biochem. J., 113:515–524 (1969).
Gilbert, et al., Biochem. J., 183:481–494 (1979).
Heath, H.B., et al., Flavor Chemistry & Technology, Chapter 9, pp. 318–331 (1986).
Huberman, et al., Proc. Nat'l. Acad. Sci. (USA), 78:3151–3154 (1981).
Huynh, T.V., et al., DNA Cloning, Chapter 2, vol. 1, pp. 49–78 (1985).
Ikegami, et al., Life Sci., 40:2277–2282 (1987).
Jackson, et al., Biochem., J., 166:1–10 (1977).
Jackson, et al., Nature, 256:331–333 (1975).
Kittler et al., Anal. Biochem., 137:210–216 (1984).
Klock, et al., Blood, 48:149–161 (1976).
Kozak, M., Nucleic Acids Res., 12:857–872 (1984).
Krishnaiah, K.V., Arch. Biochem. Biophys., 170:567–575 (1975).
Laemmli, U.K., Nature 227:680–685 (1970). [Best Copy Available].
Maclean, et al., Bio/Tech, 5:257–261 (1987).
Maniatis, et al., Molecular Cloning, Cold Spring Harbor Laboratory, pp. 315–317 and 320–321 (New York, 1982).
Messing, J., Methods Enzymol., 101:20–78 (1983).
Miyagawa, et al., Bio/Tech, 4:225–228 (1986).
Okada, et al., J. Biochem., 94:1605–1613 (1983).
Okayama, et al., Mol. Cell. Biol., 3:280–289 (1983).
Okayama, et al., Mol. Cell. Biol., 2:161–170 (1982).
Palmiter, et al., Science, 222:809–814 (1983).
Sanger, et al., Proc. Nat'l. Acad. Sci. (USA), 74:5463–5467 (1977).
Sinkar, et al., Genes & Development, 2:688–697 (1988).
Tiedeman, et al., Nucleic Acids Research, 13:1303–1316 (1985).
Towbin, et al., Proc. Nat'l. Acad. Sci. (USA), 76:4350–4354 (1979).
Ullman, B., J. Biol. Chem., 258:523–528 (1983).
Vaitukaitis, J.L., Methods Enzymol., 73:46–52 (1981).
Weber, G., Cancer Res., 43:3466–3492 (1983).
Weber, G., et al., Adv. Enzyme Regul., 18:3–26 (1980.
Yamada, et al., Biochem., 27:2193–2196 (1988).
Zassenhaus, et al., Anal. Biochem., 125:125–130 (1982).

*Primary Examiner*—John L. LeGuyader
*Attorney, Agent, or Firm*—Arnold, White & Durkee

[57] ABSTRACT

Disclosed are purified and isolated DNA sequences encoding eukaryotic proteins possessing biological properties of inosine 5'-monophosphate dehydrogenase ("IMPDH"). Illustratively, mammalian (e.g., human) IMPDH-encoding DNA sequences are useful in transformation or transfection of host cells for the large scale recombinant production of the enzymatically active expression products and/or products (e.g., GMP) resulting from IMPDH catalyzed synthesis in cells. Vectors including IMPDH-encoding DNA sequences are useful in gene amplification procedures. Recombinant proteins and synthetic peptides provided by the invention are useful as immunological reagents and in the preparation of antibodies (including polyclonal and monoclonal antibodies) for quantitative detection of IMPDH.

18 Claims, 13 Drawing Sheets

```
  1  GGGCGGTCCTCGGAGACACGGCGGGGTGTCCTGTGTTGGCCATGGCCGACTACCTGATTA   60
                                  M   A   D   Y   L   I   S

61  GTGGGGGCACGTCCTACGTGCCAGACGACGGACTCACAGCAGCTCTTCAACTGCG      120
      G   G   T   S   Y   V   P   D   D   G   L   T   A   Q   Q   L   F   N   C   G

121  GAGACGGCCTCACCTACAATGACTTTCTCATTCTCCCTGGGTACATCGACTTCACTGCAG  180
      D   G   L   T   Y   N   D   F   L   I   L   P   G   Y   I   D   F   T   A   D

181  ACCAGGTGGACCTGACTTCTGCTCTGACCAAGAAAATCACTCTCTTAAGACCCCACTGTTT 240
      Q   V   D   L   T   S   A   L   T   K   K   I   T   L   K   T   P   L   V   S

241  CCTCTCCCATGGACACAGTCACAGAGGCTGGGATGGCCATAGCAATGGCCCTTACAGGCG  300
      S   P   M   D   T   V   T   E   A   G   M   A   I   A   M   A   L   T   G   G

301  GTATTGGCTTCATCCACCACAACTGTACACCTGAATTCCAGGCCAATGAAGTTCGGAAAG  360
      I   G   F   I   H   H   N   C   T   P   E   F   Q   A   N   E   V   R   K   V

361  TGAAGAAATATGAACAGGGATTCATCACAGACCCCTGTGGTCCTCAGCCCCAAGGATCGCG  420
      K   K   Y   E   Q   G   F   I   T   D   P   V   V   L   S   P   K   D   R   V
```

FIG. 1A

```
421  TGCGGGATGTGTTTTGAGGCCCAAGGCCCGGCATGGTTTCTGCGGTATCCCAATCACAGACA   480
      R  D  V  F  E  A  K  A  R  H  G  F  C  G  I  P  I  T  D  T

481  CAGGCCCGGATGGGGAGCCGCTTGGTGGGCATCATCTCCTCCAGGACATTGATTTTCTCA     540
      G  R  M  G  S  R  L  V  G  I  I  S  S  R  D  I  D  F  L  K

541  AAGAGGAGGAACATGACTGTTTCTTGGAAGAGATAATGACAAAGAGGGAAGACTTGGTGG    600
      E  E  H  D  C  F  L  E  E  I  M  T  K  R  E  D  L  V  V

601  TAGCCCCCCGCAGCATCACACTGAAGGAGGCAAATGAAATTCTGCAGCGCAAGAAGG       660
      A  P  R  S  I  T  L  K  E  A  N  E  I  L  Q  R  S  K  K  G

661  GAAAGTTGCCCATTGTAAATGAAGATGAGCTTGTGGCCATCATTGCCCGGACAGACC        720
      K  L  P  I  V  N  E  D  D  E  L  V  A  I  I  A  R  T  D  L

721  TGAAGAAGAATCGGGACTACCCACTAGCCTCCAAAGATGCCAAGAAACAGCTGCTGTGTG    780
      K  K  N  R  D  Y  P  L  A  S  K  D  A  K  K  Q  L  L  C  G

781  GGGCAGCCATTGGCACTCATGAGGATGACAAGTATAGGCTGGACTTGCTCGCCCAGGCTG    840
      A  A  I  G  T  H  E  D  D  K  Y  R  L  D  L  L  A  Q  A  G
```

FIG. 1B

```
841  GTGTGGATGTAGTGGTTTTGGACTCTCTTCCAGGGAAATTCCATCTTCCAGATCAATATGA  900
      V  V  D  V  V  V  L  D  S  S  Q  G  N  S  I  F  Q  I  N  M  I

901  TCAAGTACATCAAAGACAAATACCCTAATCTCCAAGTCATTGGAGGCAATGTGGTCACTG  960
      K  Y  I  K  D  K  Y  P  N  L  Q  V  I  G  G  N  V  V  T  A

961  CTGCCCAGGCCAAGAACCTCATTGATGCAGGTGTGGATGCCCTGCGGGTGGGCATGGGAA  1020
      A  Q  A  K  N  L  I  D  A  G  V  D  A  L  R  V  G  M  G  S

1021 GTGGCTCCATCTGCATTACGCAGGAAGTGCTGGCCTGTGGGCGGCCCCAAGCAACAGCAG  1080
      G  S  I  C  I  T  Q  E │V  L  A  C  G  R  P  Q  A  T  A  V│

1081 TGTACAAGGTGTCAGAGTATGCACGGCGCTTTGGTGTTCCGGTCATTGCTGATGGAGGAA  1140
     │Y  K  V  S  E  Y  A  R  R  F  G  V  P  V  I  A  D  G  G  I│

1141 TCCAAAAATGTGGGTCATATTGCGAAAGCCCTTGGGGCCTCCACAGTCATGATGGG  1200
     │Q  N  V│G  H  I  A  K  A  L  G  A  S  T  V  M  M  G

1201 GCTCTCCTGGCTGCCACCACTGAGGCCCCTGGTGAATACTTCTTTTCCGATGGGATCC  1260
      S  L  L  A  A  T  T  E  A  P  G  E  Y  F  F  S  D  G  I  R
```

FIG. 1C

```
1261  GGCTAAAGAAATATCGGGTATGGGTTCTCTGATGCCATGGACAAGCACCTCAGCAGCC
       L  K  K  Y  R  G  M  G  S  L  D  A  M  D  K  H  L  S  S  Q          1320

1321  AGAACAGATATTTCAGTGAAGCTGACAAAATCAAAGTGGCCCAGGGAGTGTCTGGTGCTG
       N  R  Y  F  S  E  A  D  K  I  K  V  A  Q  G  V  S  G  A  V          1380

1381  TGCAGGACAAAGGGTCAATCCACAAATTGTCCCTTACCTGATTGCTGGCATCCAACACT
       Q  D  K  G  S  I  H  K  F  V  P  Y  L  I  A  G  I  Q  H  S          1440

1441  CATGCCCAGGACATTGGTGCCAAGAGCTTGACCCAAGTCCGAGCCATGATGTACTCTGGGG
       C  Q  D  I  G  A  K  S  L  T  Q  V  R  A  M  M  Y  S  G  E          1500

1501  AGCTTAAGTTTGAGAAGAGAACGTCCTCAGCCCAGGTGGAAGGTGGCGTCCATAGCCTCC
       L  K  F  E  K  R  T  S  S  A  Q  V  E  G  G  V  H  S  L  H          1560

1561  ATTCGTATGAGAAGCGGCTTTTTCTGAAAAGGGATCCAGCACACCTCCCTCGGTTTTTTTT
       S  Y  E  K  R  L  F                                                  1620

1621  CAATAAAAGTTTAGAAAGACCC  1642
```

FIG. 1D

Chinese hamster IMP dehydrogenase cDNA sequence and
translation, clone CIMP

```
 1   CACGGGTCCGTGCTCCTCGTTGGCCATGGCGGACTACCTGATTAGCGGAGGCACATCTTA    60
                     M  A  D  Y  L  I  S  G  G  T  S  Y

61   CGTGCCCGACGACGGGCTCACAGCGCAGCAGCTCTTCAACTGCGGGGATGGCCTCACCTA   120
      V  P  D  D  G  L  T  A  Q  Q  L  F  N  C  G  D  G  L  T  Y

121  CAACGATTTTCTCATTCTTCCTGGTATATCGACTTCACTGCCGACCAAGTGGATTTGAC   180
      N  D  F  L  I  L  P  G  Y  I  D  F  T  A  D  Q  V  D  L  T

181  CTCTGCTCTAACTAAGAAGATCACCCTGAAGACCCCACTGGTTTCCTCACCTATGGACAC   240
      S  A  L  T  K  K  I  T  L  K  T  P  L  V  S  S  P  M  D  T

241  TGTCACAGAGGCTGGAATGGCCATTGCAATGGCGCTTACAGGAGGTATTGGCTTCATCCA   300
      V  T  E  A  G  M  A  I  A  M  A  L  T  G  G  I  G  F  I  H

301  CCACAACTGTACACCTGAATTCCAGGCCAATGAAGTTCGGAAAGTAAAGAAATATGAACA   360
      H  N  C  T  P  E  F  Q  A  N  E  V  R  K  V  K  K  Y  E  Q
```

FIG. 2A

```
361  GGGATTCATAACTGATCCTGTAGTCCTTAGCCCCAAGGATCGTGTGAGGGATGTTTTTGA   420
      G  F  I  T  D  P  V  V  L  S  P  K  D  R  V  R  D  V  F  E

421  AGCCAAAGCCAGGCATGGCTTCTGTGTATCCCCATCACAGATACAGGCCGATGGGGAG    480
      A  K  A  R  H  G  F  C  G  I  P  I  T  D  T  G  R  M  G  S

481  TCGACTGGTGGGCATCATTTCTTCAAGGGATATTGATTTTCTCAAGGAGGAAGAGCATGA   540
      R  L  V  G  I  I  S  S  R  D  I  D  F  L  K  E  E  E  H  D

541  CCGTTTCTTGGAGGAGATCATGACAAAGAGGGAAGATTTGGTGGTGGCCCCTGCAGGCAT   600
      R  F  L  E  E  I  M  T  K  R  E  D  L  V  V  A  P  A  G  I

601  CACTCTGAAGGAGGCAAATGAAATTCTGCAGCGCAGTAAAAAGGGAAAGTTGCCCATTGT   660
      T  L  K  E  A  N  E  I  L  Q  R  S  K  K  G  K  L  P  I  V

661  GAATGAAAATGATGAGCTGGTAGCCATCATTGCTCGGACAGACCTGAAGAAGAATCGTGA   720
      N  E  N  D  E  L  V  A  I  I  A  R  T  D  L  K  K  N  R  D

721  TTACCCCATTGGCTTCCAAAGATGCCAAAAAGCAGCTACTATGTGGGCAGCCATTGGTAC   780
      Y  P  L  A  S  K  D  A  K  K  Q  L  L  C  G  A  A  I  G  T
```

FIG. 2B

```
781  TCATGAGGATGACAAGTATAGGCTGGACTTACTGGCTCTTGCTGGTGTGGATGTAGTGGT  840
     H   E   D   D   K   Y   R   L   D   L   L   A   L   A   G   V   D   V   V   V

841  TTTGGACTCTTCCCAGGGAAACTCCATTTCCAAATCAATATGATCAAATACATGAAAGA   900
     L   D   S   S   Q   G   N   S   I   F   Q   I   N   M   I   K   Y   M   K   E

901  GAAATACCCCAATCTCCAAGTCATTGGAGGCAATGTAGTCACTGCTGCTCAAGCCAAGAA   960
     K   Y   P   N   L   Q   V   I   G   G   N   V   V   T   A   A   Q   A   K   N

961  CCTCATAGACGCAGGTGTGTGGATGCTCTGCGAGTTGGCATGGGGTGTGGTTCCATCTGCAT  1020
     L   I   D   A   G   V   D   A   L   R   V   G   M   G   C   G   S   I   C   I

1021 TACTCAGGAAGTGTTGGCCTGTGTTGGCCGTCCAAGCAACAGCAGTGTACAAGGTTTCTGA  1080
     T   Q   E   V   L   A   C   G   R   P   Q   A   T   A   V   Y   K   V   S   E

1081 GTATGCTCGGCGCTTTGGTGTGTTCCTGTTATTGCTGATGGAGGAATCCAAAATGTGGTCA  1140
     Y   A   R   R   F   G   V   P   V   I   A   D   G   G   I   Q   N   V   G   H

1141 TATTGCCAAAGCTTTGGCTCTCTTGGAGCTTCTACAGTCATGATGGGCTCCCTCTTGGCTGC  1200
     I   A   K   A   L   A   L   G   A   S   T   V   M   M   G   S   L   L   A   A
```

FIG. 2C

```
1201  CACCACCGAAGCCCCTGGTGAGTACTTCTTCTCAGATGGGATCCGGCTAAAAAAGTACCG   1260
       T  T  E  A  P  G  E  Y  F  F  S  D  G  I  R  L  K  K  Y  R

1261  TGGTATGGGTTCTCTTGATGCCATGGACAAGCATCTCAGCAGCCAGAACCGATATTTCAG   1320
       G  M  G  S  L  D  A  M  D  K  H  L  S  S  Q  N  R  Y  F  S

1321  TGAAGCTGACAAAATCAAAGTGGCCCAAGGAGTTCAGGAGCTGTGCAGGACAAAGGGTC   1380
       E  A  D  K  I  K  V  A  Q  G  V  S  G  A  V  Q  D  K  G  S

1381  TATCCACAAGTTCGTCCCTTATTTGATTGCTGGCATCCAGCATTCCTGTCAGGACATTGG   1440
       I  H  K  F  V  P  Y  L  I  A  G  I  Q  H  S  C  Q  D  I  G

1441  TGCCAAGAGTTTAACCCAAGTCAGAGCTACTCTGGGAACTCAAGTTTGAGAA   1500
       A  K  S  L  T  Q  V  R  A  M  M  Y  S  G  E  L  K  F  E  K

1501  GAGAACATCCTCAGCTGGTGTCCACAGCCTTCATTCGTATGAGAAGCG   1560
       R  T  S  S  A  Q  V  E  G  G  V  H  S  L  H  S  Y  E  K  R

1561  GCTTTTCTGAAAAGAGATCCAGTATATGCCCTTGAATTTTTCAATAAAAGTTTTGAAAAAA   1620
       L  F
```

FIG. 2D

MOUSE IMP DEHYDROGENASE, SEQUENCE MI1.

```
  1  CGCCCCAAGGATCGTGTACGCGATGTTTTGAGGCCAAAGCCAGGCATGGCTTCTGTGGT      60
     ----+----+----+----+----+----+----+----+----+----+----+----+
     GCGGGGTTCCTAGCACATGCGCTACAAAACTCCGGTTTCGGTCCGTACCGAAGACACCA

61  ATCCCCATCACAGATACAGGCCGGATGGGGAGTCGATTGGTGTGGGCATCATCCCTCAAGG    120
     ----+----+----+----+----+----+----+----+----+----+----+----+
     TAGGGGTAGTGTCTATGTCCGGCCTACCCCTCAGCTAACCACCCGTAGTAGGAGTTCC

121  GACATTGATTCCTCAAGGAGGAAGAGCATGACCGGTTCTTGGAAGAGATCATGACTAAG     180
     ----+----+----+----+----+----+----+----+----+----+----+----+
     CTGTAACTAAGGAGTTCCTCCTTCTCGTACTGGCCAAGAACCTTCTCTAGTACTGATTC

181  AGGGAAGATTTGGTGGTCGCCCCTGCCGGCGTCACTCTGAAAGAGGCAAATGAGATTCTG    240
     ----+----+----+----+----+----+----+----+----+----+----+----+
     TCCCTTCTAAACCACCAGCGGGGACGGCCGCAGTGAGACTTTCTCCGTTTACTCTAAGAC

241  CAGCGAAGTAAAAAGGGAAAGTTGCCCATTGTGAATGAAAATGAGCTGGTAGCCATC      300
     ----+----+----+----+----+----+----+----+----+----+----+----+
     GTCGCTTCATTTTTCCCTTTCAACGGGTAACACTTACTTTTACTACTCGACCATCGGTAG

301  ATTGCCCGGACAGACCTAAAGAAGAATCGTGATTACCCCCCTGGC                    344
     ----+----+----+----+----+----+----+----+----+
     TAACGGGCCTGTCTGGATTTCTTCTTAGCACTAATGGGGACCG
```

FIG. 3A

MOUSE IMP DEHYDROGENASE, SEQUENCE MI2.

```
    CGGACCCACATTTTGGATTCCTCCATCAGCAATAACAGGAACACCAAAGCGACGGGCATA
1   ------+---------+---------+---------+---------+---------+   60
    GCCTGGGTGTAAAACCTAAGGAGGTAGTCGTTATTGTCCTTGTGGTTTCGCTGCCCGTAT

CTCAGAGACCCTTGTACACTGCTGTGGCCTTGGGCCCACAGGCCAACACTTCCTGGGT
61  ------+---------+---------+---------+---------+---------+   120
    GAGTCTCTGGAACATGTGACGACACCGGAACCCCGGGGTGTCCGGTTGTGAAGGACCCA

GATGCAGATGGAACCACTTCCCATGCCGAGCTCGCAAAGCATCTACACCTGCATCTATGAG
121 ------+---------+---------+---------+---------+---------+   180
    CTACGTCTACCTTGGTGAAGGGTACGGCTGAGCGTTTCGTAGATGTGGACGTAGATACTC

GTTCTTGGCTTGCGCAGCAGGTCGTCCACTGATGTAACGGAGGTTACTGGACATCTGACCCTATGA
181 ------+---------+---------+---------+---------+---------+   240
    CAAGAACCGAACGCGTCGTCCACTGATGTAACGGAGGTTACTGGACATCTGACCCTATGA
```

```
241 TCTCCTTGATGTATTTGATCATATTGATTTGGAAGATGGAGTTTCCCTGGAAGAGTCCA
    ----+----+----+----+----+----+----+----+----+----+----+----+ 300
    AGAGGAACTACATAAACTAGTATAACTAAACCTTCTACCTCAAAGGGACCCTTCTCAGGT

301 AAACCACTACATCCACACCAGCAAGGGCCAGTAAGTCAGCCTATACTTGTCATCCTTCAT
    ----+----+----+----+----+----+----+----+----+----+----+----+ 360
    TTTGGTGATGTAGGTGTGGTCGTTCCCGGTCATTCAGTCGGATATGAACAGTAGGAAGTA

361 GAGTGCCAATGGCTGCCCACACAGCAGTTGCTT
    ----+----+----+----+----+----+--- 393
    CTCACGGTTACCGACGGGTGTCGTCAACGAA
```

```
human     MADYLISGGTSYVPDDGLTAQQLFNCGDGLTYNDFLILPGYIDFTADQVDLTSALTKKIT    60
    1
hamster   MADYLISGGTSYVPDDGLTAQQLFNCGDGLTYNDFLILPGYIDFTADQVDLTSALTKKIT LKTPLVSSPMDTVTEAGMAIAMALTGGIGFIHHNCTPEFQANEVRKVKKYEQGFITDPVV    120
   61
          LKTPLVSSPMDTVTEAGMAIAMALTGGIGFIHHNCTPEFQANEVRKVKKYEQGFITDPVV LSPKDRVRDVFEAKARHGFCGIPITDTGRMGSRLVGIISSRDIDFLKEEEHD[CF]LEEIMT    180
  121
          LSPKDRVRDVFEAKARHGFCGIPITDTGRMGSRLVGIISSRDIDFLKEEEHD[RF]LEEIMT KREDLVVAP[RS]ITLKEANEILQRSKKGKLPIVNE[DD]ELVAIIARTDLKKNRDYPLASKDA    240
  181                 *                        *
          KREDLVVAP[AG]ITLKEANEILQRSKKGKLPIVNE[ND]ELVAIIARTDLKKNRDYPLASKDA KKQLLCGAAIGTHEDDKYRLDLLA[Q]AGVDVVVLDSSQGNSIFQINMIKYI[KD]KYPNLQVI    300
  241                                  *                         *
          KKQLLCGAAIGTHEDDKYRLDLLA[L]AGVDVVVLDSSQGNSIFQINMIKYM[EK]YPNLQVI
```

FIG. 4A

```
                                                                                360                                            420                                            480
301  GGNVVTAAQAKNLIDAGVDALRVGMG[S]GSICITQEVLACGRPQATAVYKVSEYARRFGVP
                                  *
     GGNVVTAAQAKNLIDAGVDALRVGMG[C]GSICITQEVLACGRPQATAVYKVSEYARRFGVP
361  VIADGGIQNVGHIAKALALGASTVMMGSLLAATTEAPGEYFFSDGIRLKKYRGMGSLDAM
     VIADGGIQNVGHIAKALALGASTVMMGSLLAATTEAPGEYFFSDGIRLKKYRGMGSLDAM
421  DKHLSSQNRYFSEADKIKVAQGVSGAVQDKGSIHKFVPYLIAGIQHSCQDIGAKSLTQVR
     DKHLSSQNRYFSEADKIKVAQGVSGAVQDKGSIHKFVPYLIAGIQHSCQDIGAKSLTQVR
                                                          514
481  AMMYSGELKFEKRTSSAQVEGGVHSLHSYEKRLF
     AMMYSGELKFEKRTSSAQVEGGVHSLHSYEKRLF
```

FIG. 4B

METHODS AND MATERIALS RELATING TO IMPDH AND GMP PRODUCTION

BACKGROUND OF THE INVENTION

The present invention relates generally to inosine 5'-monophosphate dehydrogenase (IMPDH) and more particularly to purified and isolated DNA sequences that encode proteins possessing the biological properties of eukaryotic IMPDH, to the expression products of these DNA sequences in transformed or transfected host cells, to recombinant and synthetic proteins and peptides having amino acid sequences based on the sequence of amino acids deduced from these DNA sequences, to antibodies specific for such proteins and peptides, to analytical procedures for the detection and quantification of such peptides and proteins and nucleic acids related thereto, to the use of IMPDH-encoding DNA sequences as selectable markers and as tools for gene amplification in recombinant hosts, and to cell lines and organisms displaying enhanced production of IMPDH and/or elevated levels of products such as guanosine monophosphate (GMP), whose synthesis in cells is dependent on the activity of IMPDH.

The enzyme IMPDH (EC 1.2.1.14) catalyzes the formation of xanthine monophosphate (XMP) from inosine monophosphate (IMP). In the purine de novo synthetic pathway, IMPDH is positioned at the branch point in the synthesis of adenine and guanine nucleotides and is thus the rate-limiting enzyme in the de novo synthesis of guanine nucleotides, such as guanosine 5monophosphate. [Weber, Cancer Res., 43:3466–3492 (1983); Weber, et al., Adv. Enzyme Regul., 18:3–26 (1980)]. Inhibition of cellular IMPDH activity results in an abrupt cessation of DNA synthesis [Franklin, et al., Biochem. J., 113:515–524 (1969); Cohen, et al., J. Biol. Chem., 256:8713–8717 (1981); and Duan, et al., Cancer Res., 47:4047–4051 (1987)] and a cell cycle block at the G1-S interface [Cohen, et al., Cancer Res., 43:1587–1591 (1983)]. Because IMPDH is essential in providing the necessary precursors for DNA and RNA biosynthesis, normal tissues that exhibit increased cell proliferation generally exhibit increased IMPDH activity [Jackson, et al., Nature, 256:331–333 (1975); Jackson, et al., Biochem. J., 166:1–10 (1977), Cooney, et al., Anal. Biochem., 130:339–345 (1983)]. Similarly, increased cell proliferation is accompanied by elevated enzyme activity in certain rat hepatomas with varied growth rates. Weber, Cancer Res., 43:3466–3492 (1983). These hepatomas manifest IMPDH activities that are disproportionately higher than those of normal tissues, suggesting that IMPDH is associated with cell proliferation and may be linked to either malignant cell transformation or tumor progression.

To investigate the role of IMPDH in growth regulation and malignancy, attempts have been made to purify the enzyme to homogeneity to allow preparation of specific antibodies thereto and to isolate IMPDH-encoding DNA.

IMPDH isolated from bacterial sources has been determined to vary widely with respect to allosteric properties, size, and subunit composition. IMPDH isolated from $E.$ $coli$ has been purified and characterized as a tetramer of identical subunits [Gilbert, et al., Biochem. J., 183:481–494 (1979); and Krishnaiah, Arch. Biochem. Biophys., 170:567–575 (1975)]. Unlike mammalian cell enzymes, the $E.$ $coli$ IMPDH enzyme is reported to be insensitive to the inhibitory effect of mycophenolic acid [Franklin, et al., Biochem. J., 113:515–524 (1969)]. In $E.$ $coli$, IMPDH has been determined to be the product of the guaB locus and the sequence of the guaB structural gene and surrounding DNA has been determined to span 1.533 kb and to code for an IMPDH subunit sequence of 511 amino acids with a calculated molecular weight 54,512 [Tiedeman, et al., Nucleic Acids Research, 13:1303 (1985)].

Miyagawa, et al., Bio/Tech., 4:225 (1986), have described the cloning of the Bacillus subtilis IMPDH gene, which, upon re-introduction into a B. subtilis strain that overproduced inosine, resulted in an increased production of guanosine, accompanied by a decreased accumulation of inosine. The IMPDH gene was localized on a 6.5 kb insert and further localized to a Hind III-partially digested 2.9 kb fragment. However, the gene was not reported to have been isolated and no information was provided with respect to the DNA sequence of the gene.

While a number of workers have reported the purification or partial purification of IMPDH from a variety of eukaryotic cell sources, including ascites cells, thymus cells, mouse LS cells, and other mammalian cells, none have been successful in obtaining substantial information about the amino acid sequence of the IMPDH protein, or in establishing the utility of anti-IMPDH antibodies in the characterization of the cellular role of IMPDH.

Eukaryotic IMPDH has been obtained from one plant and several animal species, including cowpea nodule cells [Atkins, et al., Arch. Biochem. Biophys., 236:807–814 (1985)], Yoshida sarcoma ascites cells [Okada, et al., J. Biochem., 94:1605–1613 (1983)], rat hepatoma 3924A cells [Ikegami, et al., Life Sci., 40:2277–2282 (1987) and Yamada, et al., Biochem., 27:2193–2196 (1988)] and Chinese hamster cells [Collart, et al., Mol. Cell. Biol., 7:3328–3331 (1987)]. The disclosures of the last-mentioned publication by the present inventors are specifically incorporated by reference herein. In all of these reports, denaturing polyacrylamide gel electrophoresis was used to assess purity and to estimate molecular weight. The reported molecular weight for all of the above metioned enzymes was approximately 56,000. A polyclonal antibody raised against the purified protein was prepared for the enzyme isolated from Yoshida sarcoma ascites cells, rat hepatoma 3924A cells, and Chinese hamster cells. As described in detail, infra, only in the case of the antibody prepared against the Chinese hamster enzyme was an antibody determined to be useful in examination of cellular regulation and useful in isolation of eukaryotic IMPDH-encoding DNA.

There continues to exist a need in the art for information regarding IMPDH enzymes of eukaryotic origins (especially of vertebrate and more particularly of mammalian origins) such as can be provided by the isolation, sequencing, and recombinant system utilization of DNA sequences encoding the same. The availability of such materials and information would make possible a vast array of novel systems and methodologies based thereon including methods and materials useful in production of products displaying IMPDH activity.

BRIEF SUMMARY OF THE INVENTION

The present invention provides novel purified and isolated DNA sequences encoding eukaryotic inosine 5'-monophosphate dehydrogenase (IMPDH), which have allowed for the initial determination of the primary structural conformation (i.e., amino acid sequence) of the eukaryotic protein. Specifically provided are sequences encoding human, mouse, and Chinese hamster IMPDH. Provided also are alternate DNA forms such as genomic DNA and DNA manufactured by partial or total chemical synthesis from nucleotides. The association of DNA sequences of the invention with expression regulatory DNA sequences, such as promoters, enhancers and the like, allows for in vivo and in vitro transcription to form messenger RNA, which, in turn, is subject to translation to provide IMPDH protein in large quantities.

Among the multiple aspects of the present invention, therefore, is the provision of (a) novel eukaryotic IMPDH DNA sequences as set out in FIGS. 1, 2, and 3; (b) IMPDH-encoding DNA sequences, which hybridize thereto under hybridization conditions of the stringency equal to or greater than the conditions described herein as used in the initial isolation of cDNAs of the invention, which also encode proteins with IMPDH biological activities; and (c) DNA sequences encoding the same, allelic variant and/or analog IMPDH proteins, which incorporate, at least in part, degenerate codons. Correspondingly provided are viral or circular plasmid DNA vectors incorporating such DNA sequences and prokaryotic and eukaryotic host cells transformed or transfected with such DNA sequences and vectors, as well as novel methods for the recombinant production of IMPDH proteins through cultured growth of such hosts and isolation thereof from the hosts or from their culture media.

According to another of its aspects, cell lines and organisms having enhanced production of IMPDH, as well as enhanced production of guanosine monophosphate (GMP), are also provided. Preferred embodiments of such cells include the transformed or transfected host cells described initially above. Plasmid HIMP, containing the cloned human DNA sequence as an EcoRI insert ligated into the EcoRI site of a Bluescript KS+ vector (Stratagene, LaJolla, Calif.) and transformed into E. coli DH-1 cells was deposited on Jul. 29, 1988 with the American Type Culture Collection, Rockville, Md. under A.T.C.C. accession No. 67753. Also comprehended are naturally occurring or mutagenized eukaryotic cells, which are selected for increased IMPDH production (e.g., on the basis of capacity for growth in the presence of elevated levels of cytotoxic IMPDH inhibitors) and then additionally subjected to stepwise incremental selection in the presence of a cytotoxic IMPDH inhibitor such as mycophenolic acid (MPA), ribavirin, brenidin, and tiazofurin. Illustratively, naturally occurring or mutagenized cells capable of growing in medium containing 0.1 to 0.5 μg/mL MPA are subjected to stepwise selection at increasingly higher levels of the agent.

The preparation and incorporation of IMPDH DNA sequences for use as a selectable marker to select for cells that have incorporated a selected fragment of foreign DNA into their genetic material is also embraced by the present invention. In one illustration of the DNA selection systems of the invention, Chinese hamster IMPDH encoding DNA is operatively associated in a plasmid construct with appropriate expression control sequences, and e.g., a DNA sequence coding for the E. coli gpt protein. This plasmid construct is then introduced into hamster cells, and cells functionally incorporating the IMPDH/gpt gene construct are selected on the basis of survival in culture media that contains MPA.

Novel protein products of the invention include recombinant-produced compounds having the primary structural conformation (i.e., amino acid sequence) of IMPDH protein, as well as peptide fragments thereof and synthetic peptides assembled to be duplicative of amino acid sequences thereof. Proteins, protein fragments, and synthetic peptides of the invention are projected to have numerous uses including therapeutic, diagnostic and prognostic uses and also provide the basis for the preparation of monoclonal and polyclonal antibodies specifically immunoreactive with IMPDH. Preferred protein fragments and synthetic peptides include those that duplicate continuous antigenic epitope sequences of the full-length protein.

Preferred protein products of the invention include approximately 56 kDa IMPDH peptides having the deduced sequence of 514 amino acid residues for human and Chinese hamster proteins set out in FIGS. 1 and 2. The preferred 56 kDa IMPDH polypeptide is characterized by a capacity to specifically bind IMP with a $K_i$ equal to approximately 25 μmol, a sensitivity to inhibition by IMPDH inhibitors such as mycophenolic acid, and immunoprecipitability by rabbit anti-IMPDH antisera.

Antibodies specific for the novel peptide products of the invention preferably bind with high immunospecificity to IMPDH protein, fragments, and peptides, recognizing eptitopes that are not common to other proteins.

Also provided by the present invention are novel procedures for the detection and/or quantification of the IMPDH protein, as well as the corresponding nucleic acids, e.g., DNA and mRNA, associated therewith. Antibodies of the invention may be used in known immunological procedures for quantitative detection of IMPDH protein in fluid and tissue samples. DNA sequences of the invention may be suitably labeled and used for the quantitative detection of mRNA encoding IMPDH or assessment of any genetic alteration resulting in amplification or rearrangement of the IMPDH gene.

Other aspects and advantages of the present invention will be apparent upon consideration of the following detailed description thereof, which includes illustrative examples of the practice of the invention, reference being made to the drawing wherein:

FIG. 1A, FIG. 1B, FIG. 1C, and forth the base sequence of a human species IMPDH cDNA and the deduced amino acid sequence of the protein product of expression of the sequence;

FIG. 2A, FIG. 2B, FIG. 2C, and FIG. 2D forth the base sequence of a Chinese hamster species IMPDH cDNA and the deduced amino acid sequence of the expression product thereof;

FIGS. 3A, FIG. 3B, and FIG. 3C set forth the base sequence for 737 bases of the 750 bases of a mouse species cDNA fragment; and, FIG. 4A and FIG. 4B provide a comparison of the human and Chinese hamster species IMPDH deduced amino acid sequences.

DETAILED DESCRIPTION

The following examples operate to illustrate practice of the invention in its numerous aspects. More particularly, Example 1 relates generation of cultured cell variants displaying altered levels of IMPDH activity as a result of mutagenesis and incremental selection. Example 2 relates to IMPDH purification from Chinese hamster cells and the partial purification of IMPDH from human cells. Example 3 relates to the preparation of rabbit anti-IMPDH antiserum, the isolation of IMPDH-specific IgG, and the use of this IgG in immunoblot analysis. Example 4 relates to the isolation and characterization of IMPDH cDNA from a mouse bone marrow library, a Chinese hamster library, and a human cDNA library. Example 5 relates to the protease digestion and amino terminal sequencing of the purified Chinese hamster IMPDH protein. Example 6 relates to the use of an IMPDH DNA construct as a selectable marker. Example 7 relates to the analysis of IMPDH expression in normal and in malignant cells.

The examples that follow are for illustrative purposes only and are not intended in any way to limit the scope of the invention.

EXAMPLE 1

Generation of Cell Variants with Altered IMPDH Activity

To investigate the control of IMPDH enzyme in mammalian cells, cell variants were generated from the Chinese hamster V79 line of cells according to the general procedures of Huberman, et al., *Proc. Nat'l. Acad. Sci. (USA)*, 78:3151–54 (1981).

To generate MPA-resistant cells, $4 \times 10^6$ 2- day-old exponentially growing V79 cells cultured in 100-mm Petri dishes were treated with the chemical mutagen/carcinogen N-methyl-N'-nitro-N-nitrosoguanidine (MNNG). After 3 hours of treatment, both the control and the MNNG-treated cells were dissociated with trypsin/ethylenediaminetetraacetic acid (EDTA) solution and seeded at $10^5$ cells per 100-mm Petri dish. Unless otherwise noted, the cells were dissociated 6 days later and reseeded at 200 cells per 60-mm dish in 5 mL of medium for the determination of cloning efficiency and at $2 \times 10^4$ cells per 60-mm dish in 4 mL of medium for the determination of the number of MPA-resistant cells. Two days later, MPA was added in 1 mL of medium to give a final concentration of 1 µg/mL. Thus, an expression time of 8 days was used for the selection of MPA resistance. Cloning efficiency was determined by counting the number of Giemsa-stained colonies of six to eight dishes per point at 7-8 days after cell seeding; the number of MPA-resistant cell variants was determined by counting Giemsa-stained colonies in 40 Petri dishes per point at 18–21 days after cell seeding. The frequency of the drug-resistant colonies was calculated per $10^5$ colony-forming cells based on the cloning efficiency and the number of cells seeded for mutant selection.

In addition, after a 6-day expression time, a sample of control and MNNG-treated (0.5 µg/mL) cells was incubated with MPA at 0, 0.1, and 0.3 µg/mL. Both the control and MNNG-treated cells had a similar growth rate, yielding, after 5 days of growth, means (±SD) of $5.0 \pm 0.3$, $1.4 \pm 0.2$, and $0.2 \pm 0.05 \times 10^6$ cells per Petri dish for MPA at 0, 0.1, and 0.3 µg/mL, respectively. These results indicate that control and MNNG-treated cells exhibit not only a similar growth rate but also a similar susceptibility to the cytotoxic effect of MPA.

According to the present invention, the resistance level of one of these cell variants was further increased by a stepwise selection in the presence of increasing concentrations of MPA. After adaptation to the higher concentration of MPA, the cells were seeded in medium containing an increased concentration of MPA at 200 cells per 60-mm petri dish, and MPA-resistant colonies were isolated 8 days later.

Four replications of this procedure resulted in four variants, designated VM1 through VM4, which exhibited resistance to 5, 10, 25, and 50 µg/mL MPA, respectively, whereas the parental V79 cells were resistant to only 0.1 µg/mL MPA. The increased resistance to MPA cytotoxicity in the variant cells was associated with an increased activity of IMPDH in cell homogenates, with VM1 cells exhibiting about a six-fold increase in IMPDH activity over the parental cells, and VM2, VM3, and VM4 cells expressing about 7-, 9-, and 11-fold increases in IMPDH activity, respectively.

EXAMPLE 2

IMPDH Purification from Chinese Hamster Cells and Human Cells

The generation of the IMPDH overproducing VM2 cell variant in Example 1 facilitated the isolation of a highly purified preparation of IMPDH allowing for the development of a specific anti-IMPDH antibody for subsequent cDNA cloning and immunoblot analysis.

IMPDH was isolated from VM2 Chinese hamster cells as follows. VM2 cells were scraped from the tissue culture plates, and washed with a phosphate buffer saline solution (PBS, pH 7.4, containing 137 mM NaCl, 2.6 mM g/L KCl, 1.5 mM $KH_2PO_4$, and 8 mM $Na_2HPO_4$) containing 0.5 mM phenylmethylsulfonyl fluoride (PMSF). The cells were collected by centrifugation at 800×g for 5 minutes and the pellet homogenized in 10 volumes of buffer A, pH 7.2, which contained 20 mM $KH_2PO_4$, 50 mM KCl, 0.5 mM dithiotreitol (DTT) and 0.1 mM PMSF. The cell homogenate was centrifuged at 180,000×g for 40 minutes at 4° C. The supernatant was removed and applied to a hydroxylapatite column (2.5×30 cm) equilibrated with buffer A. The column was then washed with 10 volumes of buffer A and the protein eluted with a linear gradient of 0–17.5% $(NH_4)_2SO_4$ (400 mL) in buffer A.

IMPDH activity was determined by measuring the IMP-dependent AND reduction at 37° C. by monitoring the change in absorbance at 340 nm. One unit of enzyme activity was defined as the amount of enzyme forming 1 µmole of NADH per minute at 37° C. under the prescribed assay conditions. Those fractions having enzyme activity were combined and the solution adjusted to 50% saturation with $(NH_4)_2SO_4$. After incubation of this solution at 4° C. for one hour, the precipitate was collected by centrifugation at 12,000×g for 10 minutes. The pellet was dissolved in 50 volumes of buffer B (20 mM Tris-HCl, pH 7.0, 10% glycerol, and 0.5 mM EDTA) and the solution applied to a Blue-Sepharose™ CL-6B column (1.5×20 cm) equilibrated with buffer B. The column was washed with 10 volumes of buffer B followed by 2 volumes of buffer B containing 10 mM NAD and 1 mM IMP. The enzyme was eluted with a linear gradient of 0–1M KCl in 200 mL of buffer B. Fractions with a high specific activity were combined, concentrated by ultrafiltration, and dialyzed against buffer B. The dialyzed material was applied to a DEAE Sepharose™ column (1×5 cm) equilibrated with buffer B. The column was washed with buffer B and the enzyme eluted with a linear KCl gradient (0–0.5M) in 50 mL of buffer B. Protein concentration was determined by the BCA assay method (Pierce Chemical Co., Rockford, Ill.) with bovine serum albumin used as the standard. The enzyme was purified from a microsomal supernatant to a final specific activity of 1080 mU/mg of protein in a 23% yield.

Polyacrylamide gel electrophoresis was carried out in 7.5% gels as described in Laemmli, *Nature*, 227:680–685 (1970). Upon sodium dodecyl sulfate (SDS) gel electrophoresis, the purified protein migrated as a single species with an apparent molecular weight of 56,000. Two proteins of identical molecular weight were detected by two-dimensional (2 D) gel electrophoresis. One of these proteins, constituting less than 10% of the total amount of the protein, is presumably a charge-modified form of the major species. No other proteins were detected when up to one microgram of the purified protein was analyzed by electrophoresis.

Kinetic studies were carried out by varying the substrate conditions. In all cases, linear reciprocal plots were defined by simple regression analysis of the data. The kinetic characteristics of the purified Chinese hamster protein were indistinguishable from those reported for the partially purified enzyme from V79 cells. The $K_m$ values of the Chinese hamster enzyme for IMP and NAD were calculated to be 21 and 29 µM, respectively. Moreover, the Chinese hamster enzyme retained a high sensitivity to MPA with a $K_i$ in the nanomolar range.

IMPDH was partially purified from human HL-60 cells obtained from R. C. Gallo, National Cancer Institute, Bethesda, Md., and were processed as described above with respect to Chinese hamster cells. Comparison of purified Chinese hamster protein with the partially purified human enzyme by 2D-gel electrophoresis indicates these proteins are of a similar molecular weight but that the human enzyme is slightly more acidic than the Chinese hamster enzyme. This observation was later confirmed by a comparison of the deduced amino acid sequences from the human and Chinese hamster cDNA clones (discussed infra), which indicated the human enzyme has one fewer positively charged and one additional negatively charged amino acid.

EXAMPLE 3

Preparation of Rabbit Anti-IMPDH Antiserum, Isolation of IMPDH Specific IgG, and and Development of Assay System An anti-IMPDH antiserum was prepared in rabbits by multiple-site injections of an emulsion of the purified Chinese hamster enzyme, prepared according to Example 2, and Freund's Complete Adjuvant [Vaitukaitis, *Methods Enzymol.*, 73:46–52 (1981)]. IMPDH specific IgG was isolated from the immune serum by Protein A Sepharose™ (Pharmacia Inc., Piscataway, N.J.) chromatography. By immunoblot analysis, this antibody was shown to react with IMPDH isolated from Chinese hamster, rat and human cells.

Assay systems were devised for determination of cellular IMPDH based on use of the rabbit antibody. According to these systems, target cells were washed in PBS and the cell pellet resuspended in 1–5 mL of 20 mM Tris-HCl, pH 6.8, 200 mM KCl, 1 mM DTT (buffer A). The cells were then centrifuged at 12,000×g for 8 seconds and the pellet resuspended in 1.2 mL of buffer A. After three freeze/thaw cycles to disrupt the cells, the suspension was centrifuged at 12,000×g for 10 minutes. The supernatant was removed and 3M NaAc, pH 5.2, was added to give a final concentration of 180 mM. After incubation on ice for 30 minutes, the protein precipitate was recovered by centrifugation for 10 min. in a microfuge. The IMPDH-enriched pellet was resuspended in 0.3 mL of 20 mM Tris-HCl, pH 8.3, 50 mM NaCl, 1 mM DTT. After removal of any insoluble material by centrifugation, aliquots were removed for the determination of enzyme activity and protein content and the remainder of the sample was stored at -20° C.

Western blot analyses [Towbin, et al., *Proc. Nat'l. Acad. Sci. USA*, 76:4350–4354 (1979)] were carried out with the IMPDH-specific IgG prepared from the anti-IMPDH antiserum by Protein A affinity chromatography. The detection level is approximately $1 \times 10^{-6}$ units of IMPDH, where one unit of enzyme is defined as the amount forming 1 μmol of product per minute at 37° C. under standard assay conditions. The sample is diluted with 5× gel sample buffer (6% SDS; 200 mM DTT; 300 mM Tris-HCl, pH 6.8; 0.25% bromophenol blue; 30% glycerol) and electrophoresed at 50 volts for 12–18 hours. The proteins are transferred to nitrocellulose (Scheicher and Schuell, BA83, 0.2 μm) in 50 mM Tris-HCl, 40 mM glycine, pH 8.3, 15% methanol by application of 100 mamps (20 V) for 8–12 hours. The nitrocellulose blot is incubated in TS (25 mM Tris-HCl, pH 7.5; 150 mM NaCl) with 5% nonfat dry milk for 30 minutes and then with the anti-IMPDH antibody overnight. Immune complexes were visualized by incubation with goat anti-rabbit IgG followed by incubation with rabbit IgG conjugated with horseradish peroxidase and 4-chloronapthol (3 mg/mL in 20% methanol with 0.01% $H_2O_2$), used as the substrate. [Kittler, et al., *Anal. Biochem.*, 137:210–216 (1984)].

EXAMPLE 4

Isolation and Characterization of IMPDH cDNA from Mouse Bone Marrow, Chinese Hamster, and Human cDNA Libraries The rabbit antiserum prepared according to Example 3 from the purified Chinese hamster protein was used to screen a gt11 cDNA expression library derived from mouse bone marrow [Clonetech Laboratories, Inc. (Palo Alto, Calif.)], by means of the screening procedure outlined by Huynh, et al., *DNA Cloning (Glover, D. M., ed.)* 1:73–75 (1985) IRL Press Limited, Washington, D.C. The nitrocellulose filters containing the absorbed phage proteins were incubated in TS (25 mM Tris-HCl, pH 7.5; 150 mM NaCl) with 5% nonfat dry milk for 30 minutes and then with the anti-IMPDH antibody overnight. Immune complexes were visualized as described in Example 3, supra.

A phage with a 750 bp cDNA insert was isolated from this library and the insert subsequently subcloned into a pUC8 vector designated pUC8/IMPDH5. Confirmation of this cDNA probe as having IMPDH coding sequences was obtained by translational arrest as described in Collart, et al., *Mol. Cell. Biol*, 7:3328–3331 (1987). This technique indicates the extent to which the hybridization of a cDNA probe with putatively homologous mRNA can specifically reduce the yield of the translation product. Poly(A)$^+$RNA isolated from the VM2 cells was used as a source for IMPDH mRNA. The pUC8/IMPDH5 probe effectively blocked the translation of an immunoprecipitable IMPDH product in a dose-dependent manner, thus validating the identity of the clone as a cDNA probe for IMPDH.

A Chinese hamster cDNA library (a generous gift from Victor Ling, University of Toronto, Toronto, Canada) was prepared from a CHO cell line E29Pro+(Elliott, et al., *Mol. Cell. Biol.*, 5:236–241 (1985); library construction was with the pCD vector system in *E. coli* x1776 [Okayama, et al., *Mol. Cell. Biol.*, 2:161–170 (1982); Okayama, et al., *Mol. Cell. Biol.*, 3:280–289 (1983)]. A human peripheral blood leukocyte cDNA library was purchased from Clonetech Laboratories, Inc. (Palo Alto, Calif.). Both libraries were screened with the mouse IMPDH cDNA probe by using the procedure outlined by Maniatis, et al., "Molecular Cloning", Ch. 10, pages 315–317 and 320–321; Fritsch, F. T., and Sambrook, J., eds.; (Cold Spring Rarbor, N.Y. 1982).

The nitrocellulose membranes containing the recombinant DNA were prehybridized for 2 hours at 65° C. in a phosphate buffer, pH 7.2, containing 0.5M $Na_2PO_4$, 1M NaCl, mM EDTA, 0.5% SDS and 100 μg/mL denatured sonicated salmon sperm DNA. The prehybridization solution was replaced with hybridization solution (prehybridization solution minus the DNA) containing $1 \times 10^6$ cpm/mL of $^{32}$P-labeled mouse probe, prepared as described by Feinberg, A. P., et al., *Anal. Biochem.*, 132:6–13 (1983), and the membranes incubated at 65° C. for 36 hours. The membranes were washed 3 times for 30 min. in 10 mM $NaH_2PO_4$, pH 7.4, 1 mM EDTA, 180 mM NaCl at 50° C. The membranes were dried, sealed in plastic wrap and exposed to x-ray film (Fuji RX) with an intensifying screen (Dupont Cronex "Lightning Plus") at -70° C.

Positive plaques were purified and the phage DNA isolated. Inserts of recombinant IMPDH clones were excised from the positive clones with Eco R1 restriction enzyme and isolated by an electro-elution technique as described by Zassenhaus, et al., *Anal. Biochem.*, 125:125–130 (1982). Insert homogeneity was verified by gel electrophoresis and the concentration determined by measuring the absorbance at 260 nm.

The cloned mouse, human and Chinese hamster IMPDH DNAs were inserted into an M13 vector [Messing, J., *Methods Enzymol.*, 101:20–78 (1983)] and were sequenced according to the dideoxy method [Sanger, F., et al., *Proc. Nat'l. Acad. Sci. USA*, 74:5463–5467 (1977)]. Each nucleotide sequence was read an average of four times and a minimum of once in each direction. Sequence data were compiled and analyzed by the use of the DNASTAR (Madison, Wis.) system digitizer and software and the accompanying protocols.

As illustrated in FIG. 1A, FIG. 1B, FIG. 1C and FIG. 1D the largest human cDNA clone, designated HIMP, has 1642 base pairs and contains an open reading frame corresponding to a protein of 514 amino acids with a calculated molecular weight of 56,282. A consensus poly(A) addition site (AATAAA) is located approximately 30 nucleotides from the termination codon at nucleotides 1584–1586. The sequence preceeding the ATG methionine initiation codon at position 48 is consistent with the eukaryotic initiation site consensus sequence described by Kozak, *Nucleic Acids Res.*, 12:857–872 (1984). Plasmid HIMP, containing the cloned human DNA sequence as an EcoRI insert ligated into the EcoRI site of a Bluescript KS+ vector (Stratagene, LaJolla, Calif.) and transformed into *E. coli* DH-1 cells was deposited on Jul. 29, 1988 with the American Type Culture Collection, Rockville, Md. under A.T.C.C. accession No. 67753.

As illustrated in FIG. 2A, FIG. 2B, FIG. 2C and FIG. 2D, the organization of the Chinese hamster cDNA is similar to that of the human clone and specifies a protein identical in size to the human protein, and contains the poly(A) and ATG concensus sequences.

The mouse DNA fragment was sequenced from the 5'-end of both strands, and these sequences are set forth in FIGS. 3A, 3B, and FIG. 3C and respectively. These sequences comprise 737 of the 750 nucleotide base pairs comprising the mouse cDNA. The mouse cDNA sequence(s) display a high degree of similarity to the human cDNA sequence and correspond(s) to the region spanned by nucleotides 405–1157 of the human HIMP clone.

FIG. 4A and FIG. 4B provide a comparison of the deduced amino acid sequences of the human and Chinese hamster proteins and indicates a high level of conservation of the amino acid sequence information. The non-matching amino acids are surrounded by a box with those having similar chemical properties denoted by an asterisk. Of the 514 amino acids specified by the two open reading frames, only eight amino acid differences are noted between the human and the Chinese hamster proteins. Futhermore, five out of eight of these amino acid changes are conservative with respect to the chemical nature of the amino acid. This similarity in amino acid sequence is mirrored in the DNA sequences that show an 89% identity.

Similar results are also obtained from a comparison of the sequence information derived from the mouse IMPDH cDNA, set forth in FIG. 3A, FIG. 3B and FIG. 3C and that derived from the human cDNA, set forth in FIG. 1A, FIG. 1B, FIG. 1C and FIG. 1D, wherein a 89% identity was observed. These results confirm the identity of the human, Chinese hamster, and mouse clones as those for IMPDH and demonstrate the high conservation of the amino acid sequence of the enzyme among these three species. A comparison was made between the deduced amino acid sequence of the cloned human IMPDH cDNA with all sequences in the NBRF database by using the software provided by the University of Wisconsin Genetics Computer Group [Devereux, et al., *Nuc. Acids. Res.*, 12:387–395 (1984)]. A degree of homology (score 347, 57% similarity over a stretch of 506 amino acids) was observed for the bacterial IMPDH protein. Three regions of 50 amino acids in the interior of the protein sequence show a 56–67% identity in amino acid sequence. If allowance is made for amino acids of similar chemical nature, the similarity of these three regions is approximately 78%.

The similarity of the human, mouse, and Chinese hamster proteins indicates a functional selection for conservation of amino acid sequence. The dissimilarities between eukaryotic and prokaryotic amino acid sequences are indicative of a substantial lack of homology of DNA sequence.

EXAMPLE 5

Protease Digestion and Amino Terminal Sequencing of Purified Chinese Hamster IMPDH Protein Initial attempts to sequence the purified Chinese hamster IMPDH protein indicated that the amino terminus was blocked. In an attempt to further verify the identity of clones putatively coding for the IMPDH protein obtained in Example 4, a portion of the Chinese hamster protein purified according to Example 2 was subjected to protease digestion and amino acid sequencing as follows.

A sample of the purified Chinese hamster protein in 20 mM Tris-HCl, pH 8.0, 200 mM KCl, 10 mM DTT, and 0.25% SDS was heated at 65° C. for 2 minutes. *Staphlococcus aureus* V-8 protease was added at a weight/weight ratio of protease to substrate of 1:100, and the solution was incubated at 37° C. for two hours. The sample was then chilled to 0° C. and centrifuged at 12,000×g for two minutes. The resulting peptides in the supernatant were purified by reversed-phase high-pressure liquid chromatography on a Synchropack C4 column (4.1×100 mm). Small aliquots (50 µL) containing approximately 350 pmoles of digested enzyme were loaded to minimize the effects of SDS. The peptides were eluted with a linear gradient (0–100%) of 60/39/1:acetonitrile/water/trifluoreacetic acid. Flow rate was 1 mL/min with a gradient duration of 30 minutes. Peptide peaks were collected in microfuge tubes, lyophilized, and stored at −70° C. Amino terminal sequencing was performed at the Chicago Medical School, North Chicago, Ill., by using an Applied Biosystems (Foster City, Calif.) protein sequencer, amino acid analyzer, and the accompanying protocols.

A sequence of 35 amino acids obtained by analysis of one of the peptides was compared with the protein sequence deduced from the human and Chinese hamster cDNA clones. This 35 amino acid segment, indicated by a box in FIG. 1A, FIG. 1B, FIG 1C, and FIG. 1D corresponds to deduced amino acid residues 336–370 in both the human and Chinese hamster proteins.

EXAMPLE 6

The Preparation and Use of an IMPDH DNA Construct as a Selectable Marker

This example describes the preparation and use of IMPDH DNA constructs, which permit identification of cells that have incorporated a selective fragment of foreign DNA into their genetic material. The successful practice of the procedures is based on the requirement of IMPDH as a normal constituent of the cell for cell survival and the knowledge that inhibitors of IMPDH can be cytotoxic to cells at concentrations of 0.1 to 0.5 µg/mL. Increased cellular levels of IMPDH confer resistance to IMPDH inhibitors and negate the cytotoxic effects of these agents.

DNA sequences that can be readily combined with the IMPDH DNA sequence include any DNA desired sequences that can be ligated into the plasmid construct and that will not compromise the ability of the IMPDH cDNA product to specify resistance to MPA (myophenolic acid) or to other IMPDH inhibitors. The constructs can be incorporated into cells by using standard DNA transfection technology (Davis, et al., *Molecular Biology*, 18-1:286–289; Davis, L. G., et al., eds. Science Publishing Co., Inc.; Elsevier, N.Y. 1986). After transfection, the addition of an IMPDH inhibitor to the culture medium will permit the growth of only those cells that have incorporated the construct into their genetic material. Cells that have not acquired the construct will be killed by the IMPDH inhibitor.

DNA sequences coding for the IMPDH enzyme were ligated into the pMSG plasmid (Pharmacia, Inc., Piscataway, N.J.), which contains appropriate expression sequences and the DNA sequence coding for the *E. coli* gpt protein. A SmaI-EcoRV fragment derived from the HIMP plasmid was subcloned into the SmaI site of the pMSG plasmid. This process placed the IMPDH cDNA under the control of a dexametasone-inducible mouse mammary tumor virus promoter. This plasmid construct was then introduced into V15 hamster cells (derived by mutagen treatment of Chinese hamster V79 cells and having no detectable HGPRT activity) by using the calcium phosphate DNA transfection technique described in Davis, et al., *Molecular Biology*, 18-1:286–289 (1986), supra.

After introduction of the construct into the hamster cells, mycophenolic acid (2 µg/mL) was added to the culture medium to select for those cells that had integrated the construct into their genetic material. Those cells that have integrated the construct into their genetic material produce the IMPDH enzyme and are therefore resistant to the cytotoxic effects of mycophenolic acid. A cell clone designated IMP1 was isolated; this clone was resistant to mycophenolic acid, indicating that the cells had incorporated the construct and were over-producing the IMPDH enzyme.

To verify that the resistance resulted from the incorporation of the construct, the MPA-resistant cells were successfully transferred to HAT medium. [Dulbecco's modified MEM containing 5% fetal bovine serum, aminopterin (2 µg/mL), and mycophenolic acid (25 µg/mL), and supplemented with hypoxanthine (15 µg/mL), thymidine (10 µg/mL), and xanthine (250 µg/mL)]. The ability of the cells to grow in the selective medium is attributable to the production of the *E. coli* gpt enzyme, which catalyzes the production of xanthine monophosphate from the reaction of xanthine and phosphoribosyl pyrophosphate. Presence of the enzyme compensates for the purine de novo synthetic block imposed by the presence of aminopterin and MPA. The dual resistance to mycophenolic acid and HAT selection displayed by the transformed host is evidence that the resistance is attributable to the incorporation of DNA of the plasmid construct. Growth of the cells for several generations in the absence of mycophenolic acid did not decrease the resistance of the cell clone to MPA, indicating that the construct DNA was incorporated into host chromosomal material.

The IMPDH expression in the IMP1 cell clone and the V15 parent was examined to further define the basis for the mycophenolic acid resistance. A five-fold increase in the IMPDH activity in cell homogenates was observed in the IMP1 cells relative to the V15 parent. The cellular protein in these cell homogenates was electrophoresed through polyacrylamide gels, transferred to nitrocellulose and the amount of IMPDH enzyme was quantitated by immunoblot analysis with the anti-IMPDH antiserum prepared according to Example 3. In both the V15 and IMP1 cells, the antiserum reacted with a protein of 56 kDa corresponding to IMPDH. The amount of IMPDH enzyme was approximately five-fold higher in the IMP1 cells than in the V15 parent. Furthermore, the relative gel migration distance of the two proteins was identical, suggesting the IMPDH protein produced in the IMP1 cells has the same molecular weight as the V15 enzyme.

The amount of IMPDH mRNA in the parent and transformed cell lines was quantitated by Northern blot analysis by using a human IMPDH cDNA probe, prepared according to Example 4. Total cellular RNA was isolated by disrupting cells in guanidinium lysis buffer, pH 7.0, composed of 4M guanidinium thiocyanate, 50 mM potassium acetate, 0.1M β-mercaptoethanol, and 0.5% sarcosyl. The RNA was purified by centrifugation through a CsCl cushion as described by Chrigwin, et al., *Biochemistry*, 18:5294–5299 (1979). Hybridization signals corresponding to a 2.2 kilobase message were detected in both the IMP1 and V15 cells. However, the IMP1 cells contained an additional hybridization band corresponding to a message size of approximately 2.0 kilobases. This is the approximate message size expected for transcription of IMPDH mRNA from the plasmid construct. These results show that the IMP1 cells overproduce an IMPDH enzyme that is indistinguishable, by polyacrylamide gel electrophoresis, from that produced by V15 cells, and suggest that the increased IMPDH is a result of transcription from the plasmid construct containing the human IMPDH cDNA.

The foregoing example demonstrates that the selectable marker system of the invention provides a convenient means to study and obtain a regulated expression of virtually any selected foreign DNA. Moreover IMPDH is a dominant marker and no requirement for use of deficient hosts exists.

EXAMPLE 7

Analysis of IMPDH Expression in Normal and Malignant Cells

To determine whether increased amounts of IMPDH mRNA are the cause of the elevated levels of IMPDH in tumor cells, total cellular RNA from a variety of growing human leukemic cell lines and in normal peripheral blood granulocytes and lymphocytes was examined by Northern blot analysis through the use of the human cDNA as described in Example 6.

Cells were grown in Dulbecco's modified Eagle's medium or RPMI 1640 medium supplemented with 10% fetal calf serum, penicillin (100 U/mL), streptomycin (100 µg/mL), fungizone (0.25 µg/mL), and glutamine (2 mM) in a humidified incubator supplied with a constant amount of 8% $CO_2$ in air. Peripheral blood leukocytes were isolated from freshly drawn peripheral blood by Histoplaque-1077 (Sigma Chemical Co., St. Louis, Mo.) gradient centrifugation as described in Boyum, A., *Scand. J. Clin. Lab. Invest.*, 21(97):51–55 (1968); and Klock, J. C., and Bainton, D. F., *Blood*, 48:149–161 (1976). The mononuclear fraction contained predominately lymphocytes (85–95%), with monocytes comprising the remaining percentage. Immediately after purification, the lymphocytes were resuspended in appropriate buffers for either Western blot analysis or for isolation of total cellular RNA.

A reduced level of IMPDH expression was consistently observed for the RNA isolated from lymphocytes relative to the leukemic cell lines that had markedly increased expression of a 2.2 kb transcript corresponding to the IMPDH message. A similar pattern was observed for the amounts of cellular IMPDH detected with the specific IMPDH antibody in conjunction with the Western blotting technique. These results were similar in that much higher amounts of the IMPDH protein were observed in the leukemic cells relative to the peripheral blood cells. Similar results were also obtained for measurements of the enzyme activity in these cell lines. These marked differences in the expression, amount, and activity, between the normal and leukemic cells may be associated with the absence of cell replication in the normal cells and the active proliferation of the leukemic cells.

Cultured normal human fibroblast and sarcoma cells were similarly analyzed. The differences in IMPDH expression between the normal and tumor cells were not as great as those observed between the leukemic cells and the normal peripheral blood cells. However, all of the sarcoma cells had higher levels of mRNA expression, larger amounts of the protein, and greater IMPDH activity than the normal fibroblasts. These differences may again be attributable in part to a difference in the growth rate of the various cell types because the 37-h doubling time of the normal fibroblasts is greater than that observed for the sarcoma cells. However, other factors appear to influence the IMPDH expression because an absolute correlation between IMPDH activity and cellular growth rate was not always observed for the tumor cell lines.

The foregoing illustrative examples relate, in part, to the isolation of cDNA sequences encoding mouse, Chinese hamster, and human species IMPDH proteins. Those skilled in the art will readily appreciate that the DNA and deduced amino acid sequence information provided herein make available numerous other forms of DNA sequences, such as genomic sequences obtainable by hybridization screening of genomic libraries through the use of DNA probes designed by using the sequence information of FIGS. 1A, FIG. 1B, FIG. 1C, FIG. and 1D; FIG 2A, FIG. 2B, FIG. 2C and FIG. 2D; and FIG. 3A, FIG. 3B and FIG 3C or manufactured DNA sequences synthesized from nucleic acids and potentially including alternate (degenerate) codons specifying the same amino acids, or DNA sequences comprising, e.g., part cDNA and part manufactured DNA. In a like manner, the DNA sequence information provided herein enables the isolation of other eukaryotic DNAs encoding IMPDH such as avian (chicken, turkey), fish, and mammalian (bovine, ovine, porcine) species DNAs by means of hybridization screening under appropriate stringency conditions.

The availability of the above-noted DNA sequences allows for preparation of IMPDH by in vitro transcription and translation of the DNA and for the development of a wide variety of viral or circular plasmid DNA vectors useful both for the biological amplification of the DNA and for the securing of recombinant expression of the DNA of proteins having IMPDH biological activities in prokaryotic and, especially, eukaryotic, host cells and organisms.

Well-known recombinant means for introducing genes into host cells and organisms have been described. For example, Palmiter, et al., *Science*, 222:809 (1983), have described transgenic mice containing the human growth hormone gene fused to a promoter sequence. Maclean, N., et al., *Bio/Tech.*, 5:257 (1987), have produced transgenic fish. Caplan, A., et al., *Science*, 222:815–821 (1983), described the use of a modified plasmid for use as a vector to transfer foreign genes into plants. More recently, Sinkar, V. P., et al., *Genes & Development*, 2:688–697 (1988), described transgenic tobacco plants. These recombinant means are expected to allow for the production of plant or animal organisms into which IMPDH encoding DNA has been introduced and which therefore contain increased endogenous levels of guanosine-5'-monophosphate (GMP). GMP, a natural constituent of all living materials and normally present only in trace amounts, is a member of a family of flavor potentiators commonly used as food additives. GMP enhances the taste intensity of certain flavors and can suppress the perception of a sour or bitter taste. [Heath, et al., "Flavor Chemistry and Technology", AVI Publishing Co., Westport, Conn., (1986)]. When combined with the commonly used food additive, monosodium glutamate, GMP acts synergistically to enhance flavor and it is therefore possible to enhance the taste properties of certain foods by increasing the endogeneous GMP levels. Organisms with increased levels of GMP can also provide a ready source for the isolation and extraction of GMP for use as a food additive. Studies of tissue culture cells with altered levels of IMPDH activity show an association between increased IMPDH activity and elevated GMP levels. [Ullman, *J. Biol. Chem.*, 258:523–528 (1983)]. Thus, selection for an organism with increased levels of IMPDH activity simultaneously selects for organisms with elevated tissue levels of GMP.

Microinjection and other transformation techniques are expected to readily allow for incorporation of extra copies of IMPDH encoding DNA into host cells and organisms, with exposure of the cells and organisms to inhibitors such as MPA providing a basis for selection of those cells having incorporated the desired sequences.

Cells and organisms having enhanced IMPDH production levels are, of course, also made available according to the present invention by means of the screening and selection procedures applied in Example 1. Briefly, a selected somatic or embryonic cell type is (either with or without prior exposure to mutagenic influences) screened in culture for the capacity to survive in the presence of elevated levels of an inhibitor such as MPA. Cells capable of surviving in the screening environment, e.g., at levels of MPA of 0.5 to 1.0 µL/mL, are thereafter subjected to stepwise incremental selection at much higher levels of the inhibitor. The resulting cells and organisms having enhanced IMPDH synthetic capacity vis-a-vis parent cells will also be expected to display enhanced capacity for synthesis of GMP.

Among the additional forms of DNA provided by the invention are those that encode allelic variants of the specific mammalian IMPDH protein of FIG. 1A, FIG. 1B, FIG 1C, and FIG. 1D; FIG. 2A, FIG. 2B, FIG. 2C, and FIG. 2D as well as analog proteins that possess one or more variations in IMPDH biological activities.

Protein and peptide products of the invention include not only those produced as recombinant expression products of "full-length" and fragmentary DNA sequences of the invention but also those that are prepared by chemical synthesis from amino acids. As one example, analysis of the deduced amino acid sequences of IMPDH proteins is expected to provide valuable information concerning potential antigenic epitopes present therein, allowing for the preparation of synthetic antigenic peptides duplicative of about 6 to 20 continuous residues of the protein. These, in turn, are expected to allow for the preparation of monospecific polyclonal and monoclonal antibodies useful in the quantitative detection of IMPDH proteins. Further, it is ancipated that the deduced amino acid sequences information can be used to modify existing drugs and to design new drugs as inhibitors of IMPDH activity.

Numerous modifications and variations in the invention as described in the above illustrative examples are expected to occur to those skilled in the art; consequently, only such limitations as appear in the appended claims should be placed thereon.

Accordingly, it is intended in the appended claims to cover all such equivalent variations that come within the scope of the invention as claimed.

What is claimed is:

1. A purified and isolated nucleic acid segment or its complement comprising at least 20 nucleotides in common with the nucleotide sequence of FIG. 1A, FIG. 1B, FIG. 1C and FIG. 1D; FIG. 2A, FIG. 2B, FIG. 2C, and FIG. 2D; or FIG. 3A, FIG. 3B, and FIG. 3C when aligned sequentially, the segment capable of hybridizing to the sequence shown in FIG. 1A, FIG. 1B, FIG. 1C, and FIG. 1D; FIG. 2A, FIG. 2B, FIG. 2C and FIG. 2D; or FIG. 3A, FIG. 3B, and FIG. 3C under stringent conditions.

2. The nucleic acid segment of claim 1 further defined as encoding the same sequence of amino acids as that shown in FIG. 1A, FIG. 1B, FIG. 1C, and FIG. 1D; FIG. 2A, FIG. 2B, FIG. 2C and FIG. 2D; or FIG. 3A, FIG. 3B, and FIG. 3C.

3. The nucleic acid segment of claim 1 further defined as a hybridization probe.

4. The nucleic acid segment of claim 1 further defined as encoding IMPDH.

5. A purified and isolated nucleic acid segment encoding the same sequence of amino acids as shown in FIG. 1A, FIG. 1B, FIG. 1C, and FIG. 1D; FIG. 2A, FIG. 2B, FIG. 2C, and FIG. 2D; or FIG. 3A, FIG. 3B, and FIG. 3C.

6. The nucleic acid sequence according to claim 4 encoding human IMPDH.

7. The nucleic acid sequence according to claim 4 encoding mouse IMPDH.

8. The nucleic acid sequence according to claim 4 encoding Chinese hamster IMPDH.

9. The nucleic acid sequence according to claim 4 which is a cDNA sequence.

10. The nucleic acid sequence according to claim 4 which is a manufactured DNA sequence.

11. A prokaryotic or eukaryotic host cell transformed or transfected with a nucleic acid sequence according to claim 1.

12. The prokaryotic or eukaryotic host cell according to claim 11 wherein said host cell is a Chinese hamster cell.

13. The prokaryotic or eukaryotic host cell according to claim 11 wherein said host is an $E.\ coli$ DH-1 cell having A.T.C.C. accession No. 67753.

14. The host cell according to claim 11 having an enhanced capacity for production of IMPDH.

15. A viral or circular nucleic acid plasmid vector comprising an IMPDH encoding nucleic acid sequence according to claim 4.

16. The vector according to claim 15, further comprising an expression control DNA sequence operatively associated with said IMPDH encoding nucleic acid sequence.

17. A method for the production of IMPDH comprising:

growing under suitable culture conditions, a host cell transformed or transfected with a nucleic acid sequence according to claim 4; and isolating from said host or its culture medium the polypeptide product of the expression of said nucleic acid sequence in said host.

18. A method for the production of IMPDH comprising:

disposing a nucleic acid sequence according to claim 4 in a cell-free transcription and translation system; and isolating from said system the polypeptide product of the expression of said sequence.

* * * * *

UNITED STATES PATENT AND TRADEMARK OFFICE
CERTIFICATE OF CORRECTION

PATENT NO.  :  5,665,583

DATED       :  September 9, 1997

INVENTOR(S) :  Frank R. Collart and Eliezer Huberman

It is certified that error appears in the above-identified patent and that said Letters Patent is hereby corrected as shown below:

In the title page, please insert item [73], --Arch Development Corporation-- as Assignee.

Signed and Sealed this

Twenty-fourth Day of March, 1998

Attest:

BRUCE LEHMAN

Attesting Officer

Commissioner of Patents and Trademarks